(12) United States Patent
Shue et al.

(10) Patent No.: US 8,303,540 B2
(45) Date of Patent: Nov. 6, 2012

(54) PRE-FILLED DISPOSABLE SYRINGE

(76) Inventors: Ming-Jeng Shue, Taichung (TW); Phillip Shue, Taichung (TW); Deborah Huang, Taichung (TW)

( * ) Notice: Subject to any disclaimer, the term of this patent is extended or adjusted under 35 U.S.C. 154(b) by 702 days.

(21) Appl. No.: 12/152,801

(22) Filed: May 15, 2008

(65) Prior Publication Data

US 2009/0124971 A1 May 14, 2009

(30) Foreign Application Priority Data

Nov. 12, 2007 (TW) .............................. 96142665 A

(51) Int. Cl.
*A61M 5/00* (2006.01)
(52) U.S. Cl. ...................................................... 604/110
(58) Field of Classification Search .................. 604/222, 604/110, 194, 198, 111, 121, 125, 192
See application file for complete search history.

(56) References Cited

U.S. PATENT DOCUMENTS

2006/0111671 A1* 5/2006 Klippenstein ................. 604/110
2008/0119786 A1* 5/2008 Stewart et al. ................ 604/110

* cited by examiner

*Primary Examiner* — Nicholas Lucchesi
*Assistant Examiner* — Weng Lee
(74) *Attorney, Agent, or Firm* — Kilpatrick Townsend & Stockton LLP

(57) ABSTRACT

A disposable syringe includes a barrel with a bushing unit disposed on an inner surrounding surface thereof, a tubular grip unit in fluid-tight engagement with the bushing unit for holding a needle seat, a tubular plunger having a seal ring that is slidable on and in fluid-tight frictional engagement with the bushing unit so as to cooperate with the grip unit to define a medicament chamber, and a shield plug member in fluid-tight engagement with the grip unit and having a duct that communicates a needle cannula with the medicament chamber, thereby ensuring fluid-tightness of the medicament chamber.

20 Claims, 15 Drawing Sheets

PRE-FILLED DISPOSABLE SYRINGE

CROSS-REFERENCE TO RELATED APPLICATION

This application claims priority of Taiwanese publication No. 096142665, filed on Nov. 12, 2007.

BACKGROUND OF THE INVENTION

1. Field of the Invention

This invention relates to a disposable syringe, more particularly to a pre-filled disposable syringe for facilitating injection and needle retraction operations with one hand.

2. Description of the Related Art

In U.S. Pat. No. 6,221,055 B1 for a retractable dental syringe, there is disclosed a pre-filled syringe, which includes a barrel, a carpule and plunger assembly that is filled with medication and that is inserted into the barrel from a rear opened end of the barrel and that is communicated with a needle by the carpule is punctured by a rear tip end of the needle, and a push ring for holding the needle in the barrel. At the end of an injection, the plunger is further pressed to move the carpule forwardly so that the push ring is removed to permit retraction of the needle. However, the carpule cannot be accommodated in the barrel in advance, and the carpule and the barrel have to be packed separately for subsequent assembly in use, thereby resulting in increased operation time. In addition, such a syringe structure makes the manufacture of the syringe complicated.

Therefore, in U.S. patent application Ser. No. 11/601,526, the applicants disclosed a disposable syringe with a built-in carpule, which includes a carpule that can be pre-assembled in a barrel so that clinical injection operation by health care workers is simplified and is convenient to conduct. Moreover, after injection, the syringe can be conveniently rendered unreusable after injection, and injection and needle retraction can be conducted smoothly in a single operation.

It is desirable to improve the aforesaid syringe to ensure air- and water-tightness of a medicament chamber so as to eliminate risk of degradation of a medicament contained therein, and to simplify the construction of the syringe.

SUMMARY OF THE INVENTION

The object of the present invention is to provide a disposable syringe which can maintain air- and water-tightness of a medicament chamber to eliminate risk of degradation of a medicament contained therein, and which has a simple construction to achieve cost savings.

According to this invention, the disposable syringe includes a barrel, a bushing unit, a needle cannula, a tubular grip unit, a tubular needle seat, a shield plug member, and a tubular plunger.

The barrel has a surrounding barrel wall defining a passage therein. The passage has rearward and forward openings. The surrounding barrel wall includes a larger-diameter portion and a smaller-diameter portion, and a shoulder abutment disposed on the smaller-diameter portion and confronting rearwardly.

The bushing unit is disposed on the larger-diameter portion, and includes front and rear bushing members that extend towards each other to terminate at front and rear retaining segments, respectively.

The needle cannula has a fixed segment extending in the passage to terminate at a communicating end, and a tip end extending forwardly of the forward opening.

The tubular grip unit includes front and rear grip members which respectively have front and rear outer surrounding retained surfaces that, in a position of use, are respectively in fluid-tight engagement with the front and rear retaining segments, by virtue of first and second frictional forces, respectively, and which respectively further have front and rear inner surrounding grip surfaces that respectively define front and rear bores.

The tubular needle seat includes a front hub portion which is disposed to fix the needle cannula therein and which has a front end wall that confronts the shoulder abutment, and a rear gripped portion extending rearwardly to terminate at an embedded end. The rear gripped portion is inserted into the front bore, and is in frictional engagement with the front inner surrounding grip surface.

The shield plug member is made from a material different from that of the tubular needle seat, and is inserted into the rear bore. The shield plug member includes a plug body and an anchored end. The plug body extends forwardly to terminate at a dock end that admits entry of the communicating end of the needle cannula, and is configured to stuff the rear bore so as to be in fluid-tight engagement with the rear inner surrounding grip surface. The anchored end has a duct configured to permit fluid communication between the anchored end and the communicating end.

The tubular plunger is movable along the passage in the bushing unit, and includes a plunger body, a seal ring, and a coupling member. The plunger body has front and rear opened end walls, and an intermediate surrounding wall defining an accommodation chamber. The seal ring is sleeved retainingly on the front opened end wall, and is slidable on and in fluid-tight frictional engagement with the rear bushing member so as to cooperate with the rear grip member to define, in the passage, a medicament chamber that is communicated with the duct. The coupling member has a retained portion disposed in the accommodation chamber to be in frictional engagement with the intermediate surrounding wall by virtue of a third frictional force, and an anchoring portion that is engageable with the anchored end when the coupling member is moved forwardly. When the front and rear grip members are pushed forward by virtue of forward movement of the plunger against the first and second frictional forces, the anchoring portion is brought to mate with the anchored end, which remains unmoved and stays in place due to abutment of the front hub portion against the shoulder abutment. Once the plunger is moved further forward to cause movement of the plunger body relative to the coupling member against the third frictional force, the retained portion is released from the intermediate surrounding wall to thereby permit movement of the anchored end with the anchoring portion to a retracted position, where the anchoring portion is disposed closer to the rear opened end wall and where the needle seat, the shield plug member and the needle cannula are received in the accommodation chamber.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
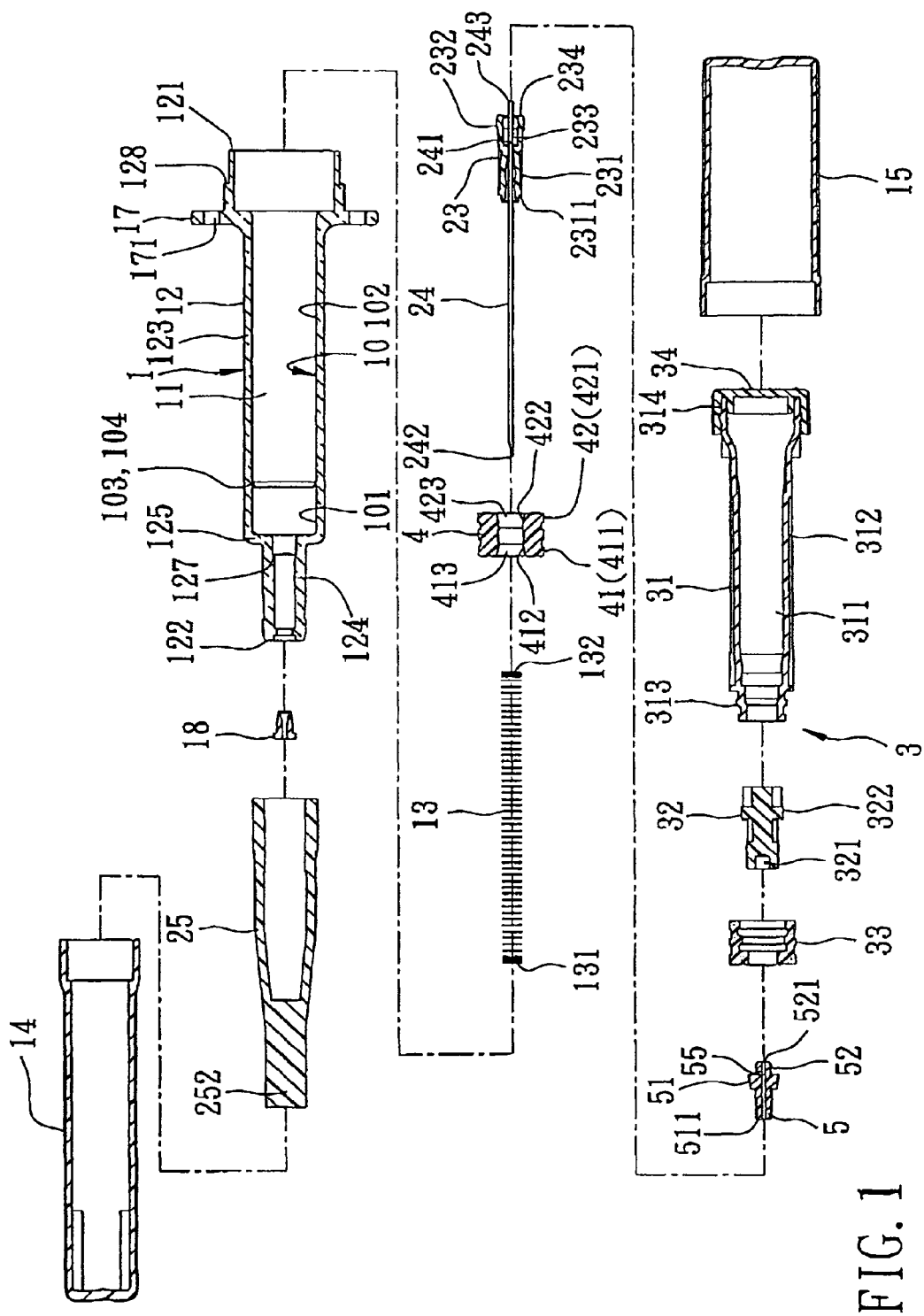
FIG. 1 is an exploded sectional view of the first preferred embodiment of a disposable syringe according to this invention.

Before the present invention is described in greater detail, it should be noted that same reference numerals have been used to denote like elements throughout the specification.

Figure 2:
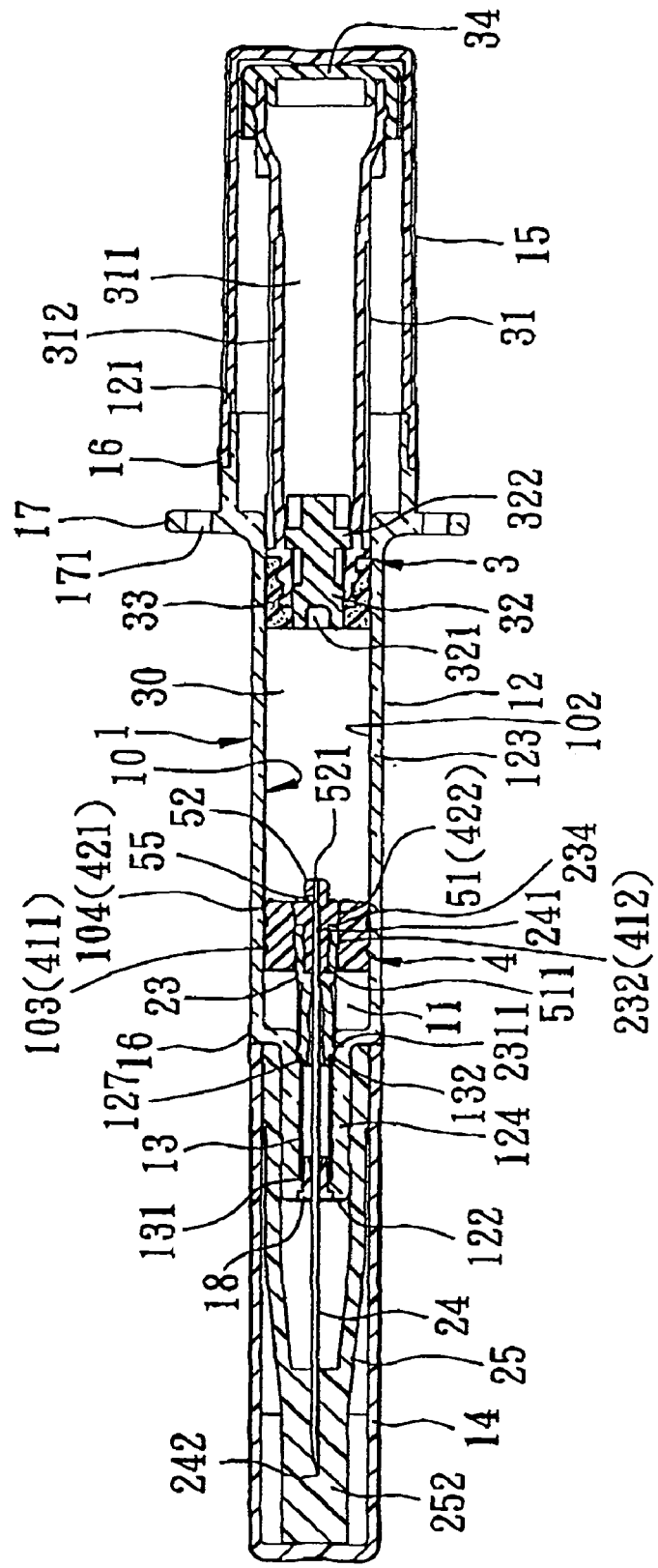
FIG. 2 is a sectional view of the first preferred embodiment in assembly.
Figure 3:
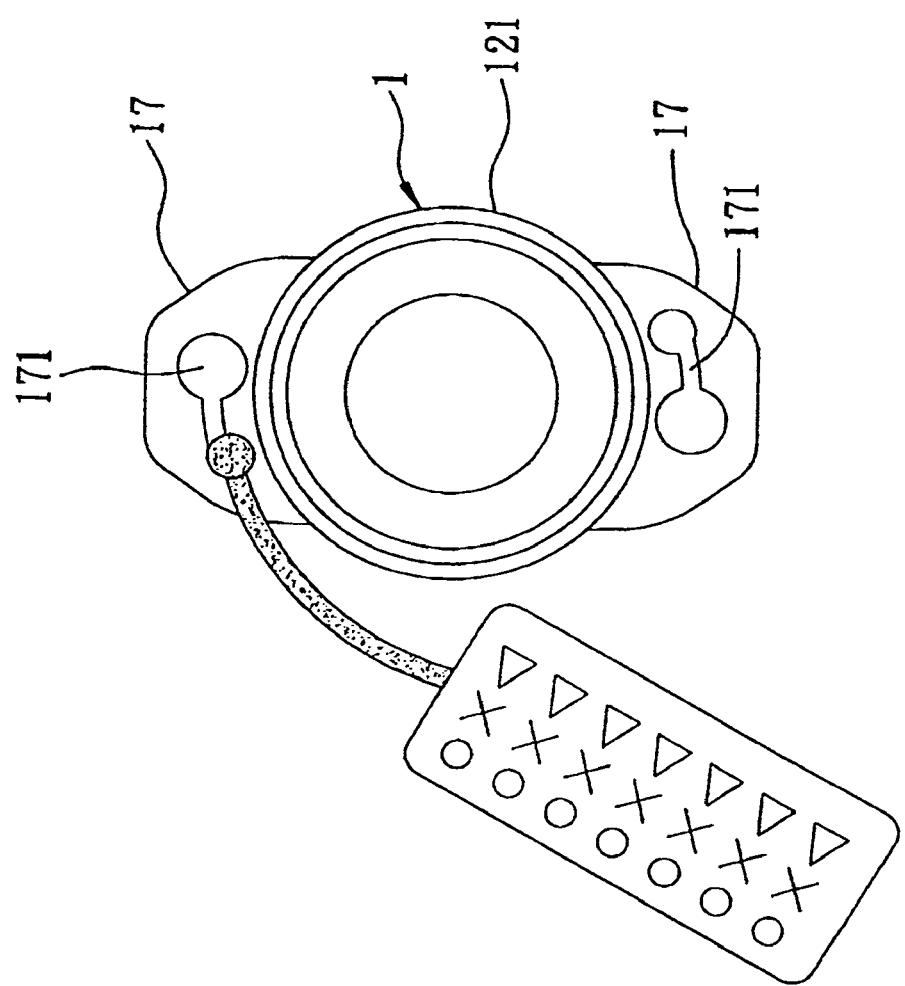
FIG. 3 is a rear view of a pair of finger flanges of the first preferred embodiment.

Referring to FIGS. 1 to 3, the first preferred embodiment of a disposable syringe according to the present invention is shown to comprise a barrel 1, a bushing unit 10, a needle cannula 24, a tubular grip unit 4, a tubular needle seat 23, a shield plug member 5, a tubular plunger 3, a coil spring 13, and front and rear protectors 14,15.

The barrel 1 has a surrounding barrel wall 12 which surrounds an axis in an axial direction, and which defines a passage 11 therein. The passage 11 has rearward and forward openings 121,122 which are disposed opposite to each other in the axial direction. The surrounding barrel wall 12 includes a larger-diameter portion 123 and a smaller-diameter portion 124 which are disposed proximate to the rearward and forward openings 121,122, respectively. The smaller-diameter portion 124 has a first shoulder abutment 127 confronting rearwardly A second shoulder abutment 125 is formed between the smaller-diameter portion 124 and the larger-diameter portion 123, and confronts forwardly. The larger-diameter portion 123 has a third shoulder abutment 128 which is disposed adjacent to the rearward opening 121 and which confronts rearwardly. A pair of lugs 17 extend radially and outwardly from the larger-diameter portion 123 adjacent to the rearward opening 121 for gripping by user's fingers, and has anchor holes 171 for anchoring a marked tab, as shown in FIG. 3, which indicates the name and amount of a medicament, the name of a patient, etc.

The bushing unit 10 is disposed on the larger-diameter portion 123, and includes front and rear bushing members 101,102 that are proximate to and distal from the first shoulder abutment 127, respectively, and that extend towards each other to terminate at front and rear retaining segments 103, 104, respectively.

In this embodiment, the front and rear bushing members 101, 102 are integrally formed with each other to constitute the bushing unit 10. The bushing unit 10 is integrally formed with the larger-diameter portion 123, and is made from a glass material, or a thermoplastic macromolecular material with chemical resistance, such as a cyclic olefin polymer or the like.

The needle cannula 24 extends along the axis and has a fixed segment 241 that extends in the passage 11 to terminate at a communicating end 243, and a tip end 242 extending forwardly of the forward opening 122. In addition, a tubular holding member 18 is inserted into the passage 11 from the forward opening 122 of the barrel 1 to be fitted to the smaller-diameter portion 124, and is configured to hold the needle cannula 24 in a position of use. An air-tight sleeve 25 is removably sleeved on the smaller-diameter portion 124 to shield the needle cannula 24, and has an elastomeric front end 252 such that the tip end 242 of the needle cannula 24 is trapped in the elastomeric front end 252.

Figure 8:
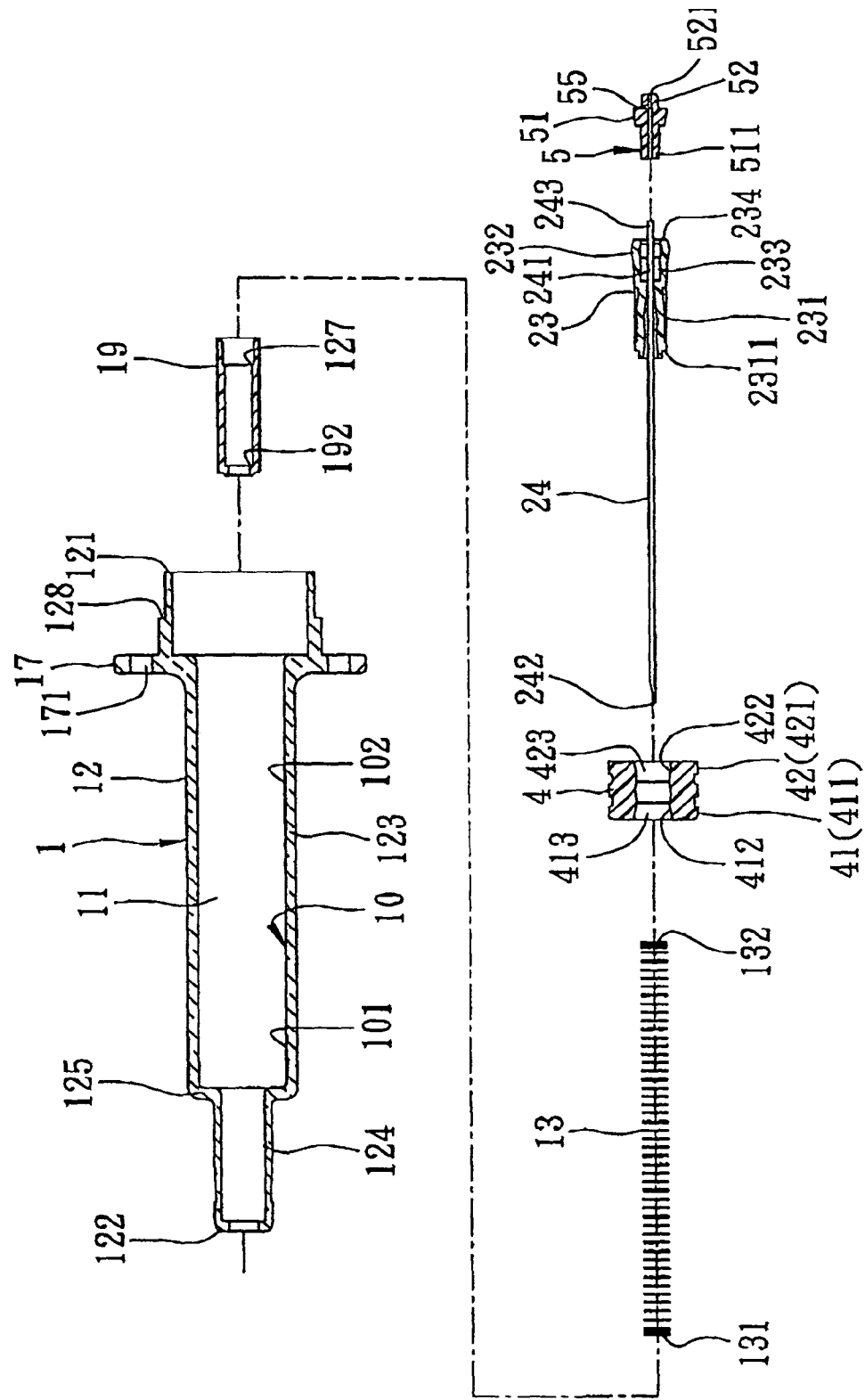
FIG. 8 is a sectional view of the second preferred embodiment of a disposable syringe according to this invention.
Figure 9:
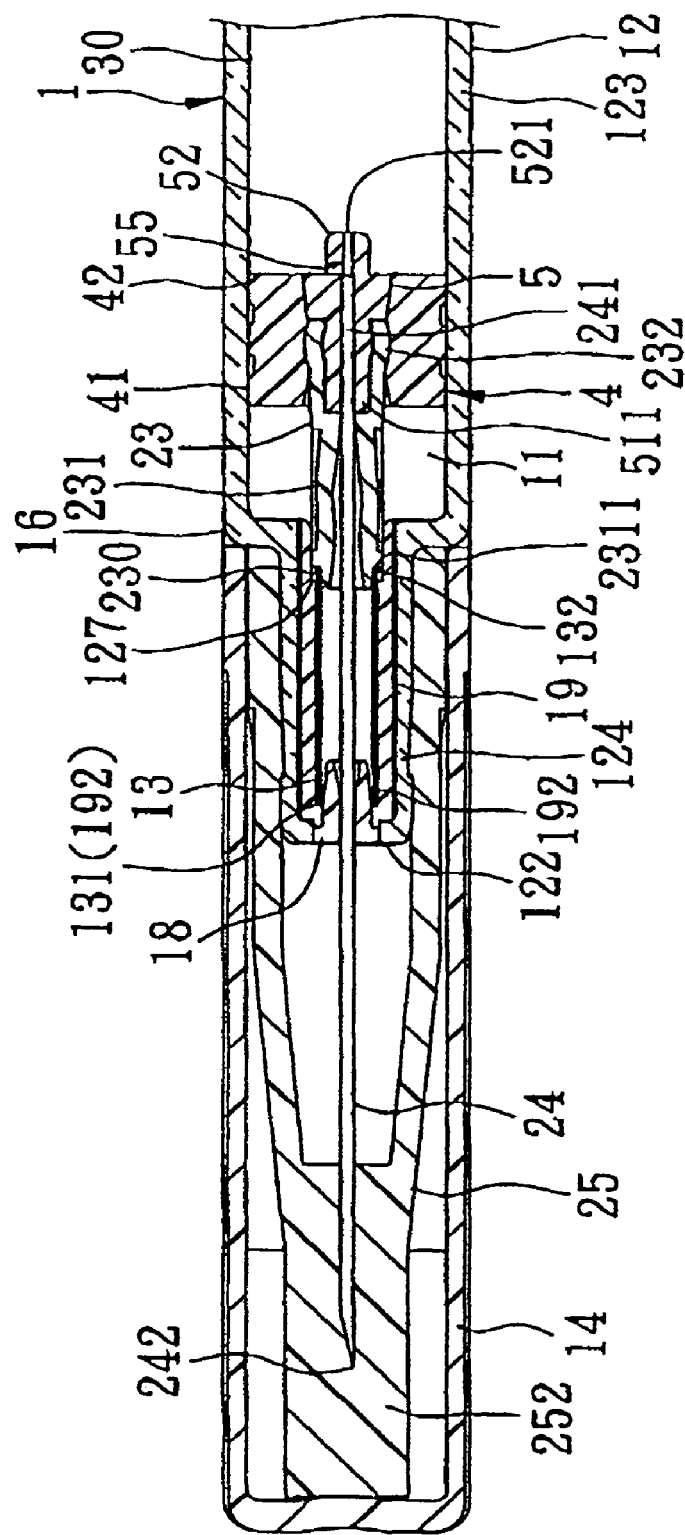
FIG. 9 is a fragmentary sectional view of the second preferred embodiment in a state of use.
Figure 10:
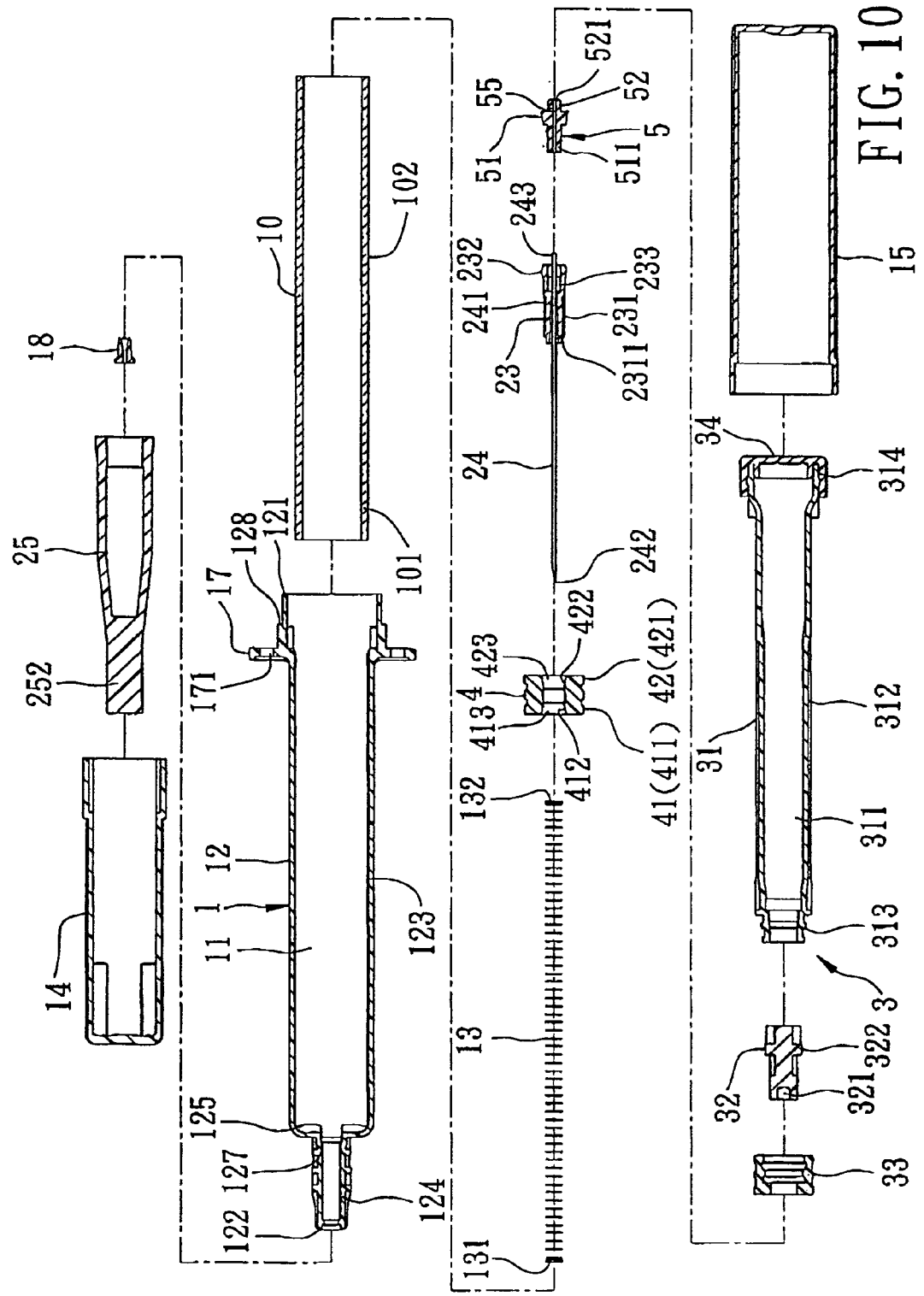
FIG. 10 is an exploded sectional view of the third preferred embodiment of a disposable syringe according to this invention.

The tubular grip unit 4 includes front and rear grip members 41,42 which are opposite to each other in the axial direction, which respectively have front and rear outer surrounding retained surfaces 411,421 that, in the position of use, are respectively in air and water-tight engagement with the front and rear retaining segments 103,104, by virtue of first and second frictional forces, respectively, and which respectively have front and rear inner surrounding grip surfaces 412,422 that respectively extend along the axis to define front and rear bores 413,423, respectively. In this embodiment, the front and rear grip members 41,42 are integrally formed with each other. Specifically, the barrel 1 is made from a thermoplastic material, and the front and rear retaining segments 103,104 are formed with a protruding ring such that the front and rear outer surrounding retained surfaces 411,421 of the tubular grip unit 4 are retainingly secured to the protruding ring. Alternatively, the barrel 1 may be made from a glass material so as to have a smooth inner wall surface, and the tubular grip unit 4 is press-fitted to the front and rear retaining segments 103,104, which are not formed with the protruding ring (as shown in FIGS. 8 to 10).

The tubular needle seat 23 includes a front hub portion 231 which is disposed to fix the needle cannula 24 therein and which has a front end wall 2311 that confronts the first shoulder abutment 127, and a rear gripped portion 232 extending from the front hub portion 231 in the axial direction to terminate at an embedded end 234. The rear gripped portion 232 is inserted into the front bore 413, and is in frictional engagement with the front inner surrounding grip surface 412.

The shield plug member 5 is made from a material different from that of the tubular needle seat 23, and is inserted into the rear bore 423. The shield plug member 5 includes a plug body 51 and an anchored end 52. The plug body 51 extends forwardly to terminate at a dock end 511. In this embodiment, the embedded end 234 of the needle seat 23 is disposed to surround the dock end 511 in the rear bore 423 such that the dock end 511 admits entry of the communicating end 243 of the needle cannula 24. The dock end 511 is configured to stuff the rear bore 423 such that the plug body 51 is in fluid-tight engagement with the rear inner surrounding grip surface 422. The anchored end 52 extends rearwardly from the plug body 51, and has a duct 521 configured to extend in the axial direction to permit fluid communication between the anchored end 52 and the communicating end 243 in the position of use. Specifically, the anchored end 52 is in the form of a plug which is disposed rearwardly and outwardly of the rear grip member 42. In addition, the anchored end 52 is provided with a radial inlet 55 which extends radially to be communicated with the communicating end 243 of the needle cannula 24, and which is disposed adjacent to the rear grip member 42.

The tubular plunger 3 is disposed to be movable along the passage 11 in the bushing unit 10, and includes a plunger body 31, a seal ring 33, and a coupling member 32. The plunger body 31 has front and rear opened end walls 313,314 which are disposed opposite to each other along the axis. The rear opened end wall 314 extends outwardly of the rearward opening 121 so as to be manually operable. The plunger body 31 further has an intermediate surrounding wall 312 which is interposed between the front and rear opened end walls 313, 314 and which defines an accommodation chamber 311. An end cap 34 is disposed to cover the rear opened end wall 314. Preferably, the accommodation chamber 311 may contain fluid at a reduced pressure.

The seal ring 33 is made from a deformable material, is sleeved retainingly on the front opened end wall 313, and is slidable on and in fluid-tight frictional engagement with the rear bushing member 102 so as to cooperate with the rear grip member 42 to define in the passage 11 a medicament chamber 30 that is communicated with the duct 521.

The coupling member 32 has a retained portion 322 that extends along the axis and that is disposed in the accommodation chamber 311 to be in frictional engagement with the intermediate surrounding wall 312 by virtue of a third frictional force, and an anchoring portion 321 extending forwardly from the retained portion 322. Specifically, the anchoring portion 321 is inform of a socket so as to mate with the plug-like anchored end 52 when the coupling member 32 is moved forwardly.

Figure 5:
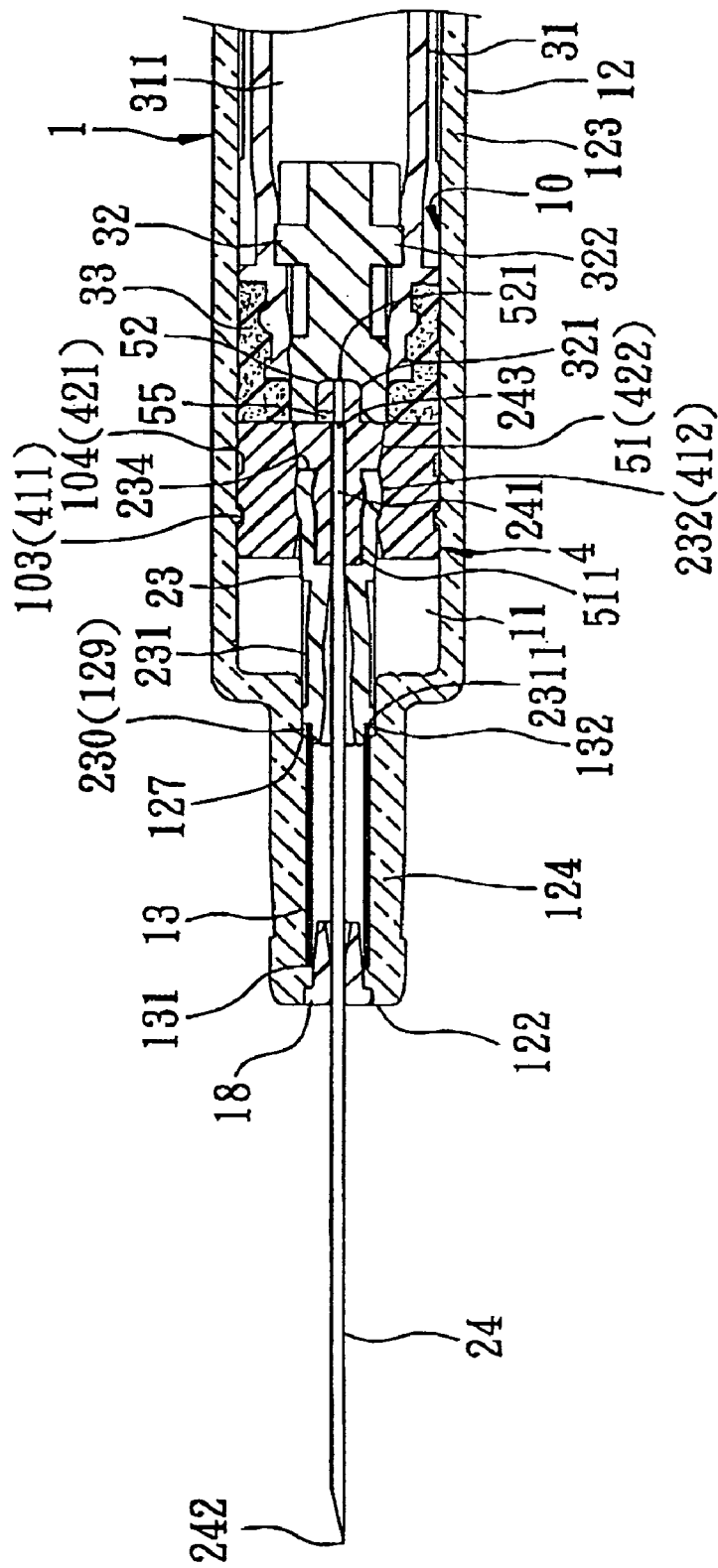
FIG. 5 is a fragmentary sectional view of the first preferred embodiment in a state after a medicament injection is completed.

Preferably, as shown in FIG. 5, the smaller-diameter portion 124 has a friction diminishing area 129 which is disposed between the first shoulder abutment 127 and the front hub portion 231 of the needle seat 23.

The coil spring 13 is disposed within the smaller-diameter portion 124 to surround the needle cannula 24, and has two spring ends 131,132 which respectively abut against the smaller-diameter portion 124 and the front end wall 2311 so as to bias the needle seat 23, together with the shield plug member 5 to move rearwardly.

The front protector 14 is detachably sleeved on the smaller-diameter portion 124, and abuts against the second shoulder abutment 125 for shielding the air-tight sleeve 25. The rear protector 15 is detachably sleeved on the larger-diameter portion 123, and abuts against the third shoulder abutment 128 for shielding the plunger 3. Front and rear sealing strips 16 are disposed to peelably adhere the front protector 14 to the second shoulder abutment 125, and to peelably adhere the rear protector 15 to the larger-diameter portion 123, respectively. Preferably, the elastomeric front end 252 of the air-tight sleeve 25 is threadedly engaged with the front protector 14.

It is noted that the barrel 1, the coupling member 32, the seal ring 33, the tubular grip unit 4, and the shield plug member 5 are made from a chemically resistant material, and cooperatively define the medicament chamber 30 so that the medicament chamber 30 has good air-tightness and water-tightness, and can ensure the quality of the medicament contained therein.

Figure 4:
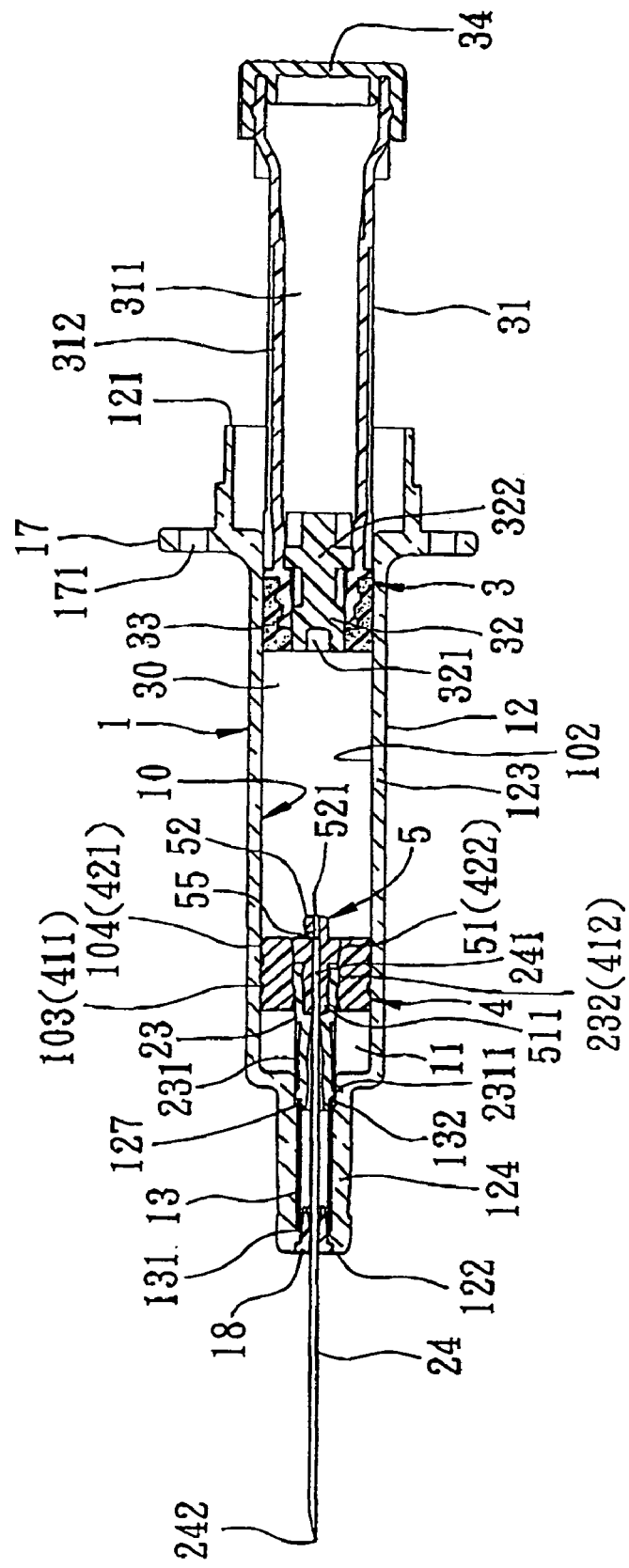
FIG. 4 is a sectional view of the first preferred embodiment in a state of use.

Referring to FIGS. 2, 4 and 5, during an injection stroke, the front and rear protectors 14,15 are removed first to expose the needle cannula 24 and the plunger body 31. The operator then holds the lugs 17 with his/her index and middle fingers and presses the plunger body 31 forwardly with his/her thumb such that the coupling member 32 and the seal ring 33 are moved forwardly along the rear bushing member 102 to expel air from the barrel 1 and accurately adjust a dosage of medicament within the barrel 1. The medicament is in turn introduced into the patient through the duct 521, the radial inlet 55 and the needle cannula 24. Subsequently, a pushing force is applied to the plunger body 31 to bring the seal ring 33 into abutment against the grip unit 4, thereby completing the injection stroke, as shown in FIG. 5. At this time, the anchoring portion 321 is fittingly engaged with the anchored end 52 for preventing dripping of the medicament.

It is noted that, during the injection operation, the radial inlet 55 can remain open when the socket-like anchoring portion 321 is brought to substantially engage the plug-like anchored end 52 to interrupt axial communication between the duct 521 and the medicament chamber 30 so as to dispense the entire amount of medicament in the medicament chamber 30.

Figure 6:
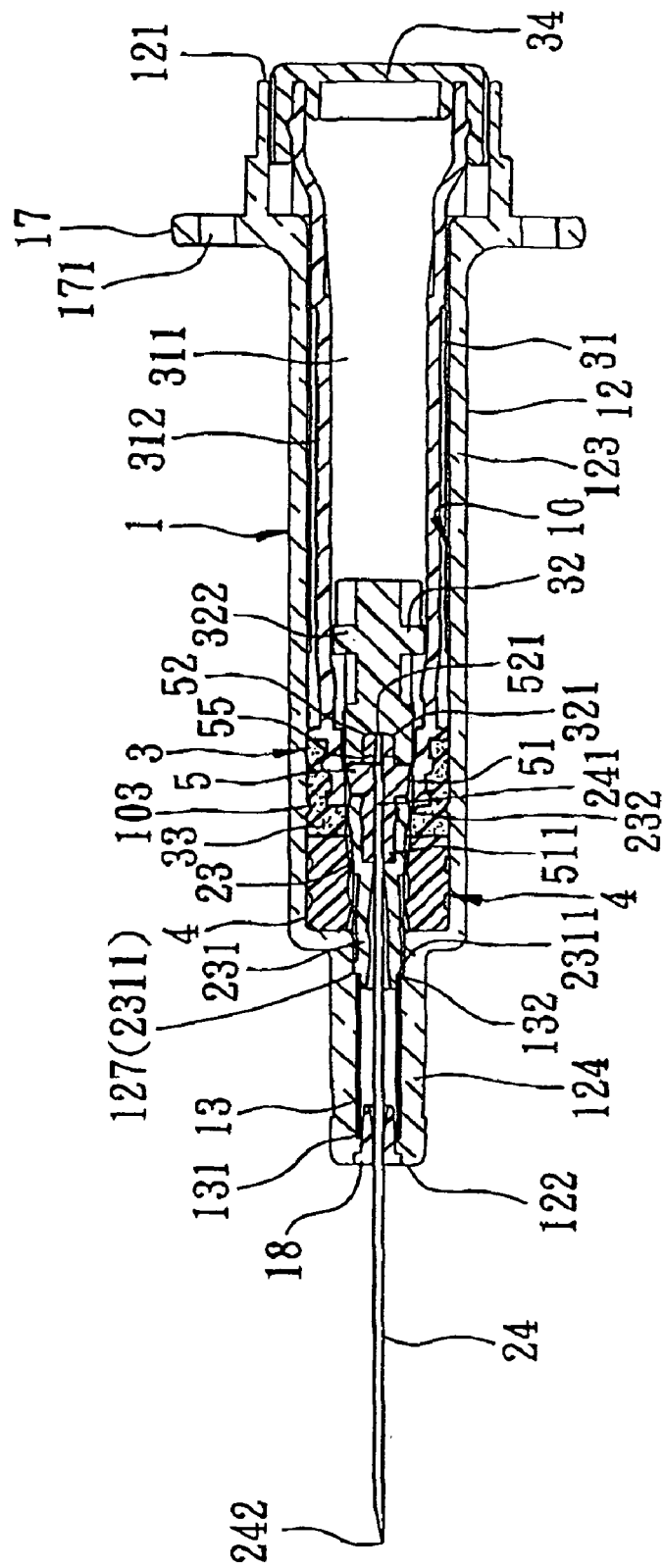
FIG. 6 is a sectional view of the first preferred embodiment when a needle seat is released from a grip unit.
Figure 7:
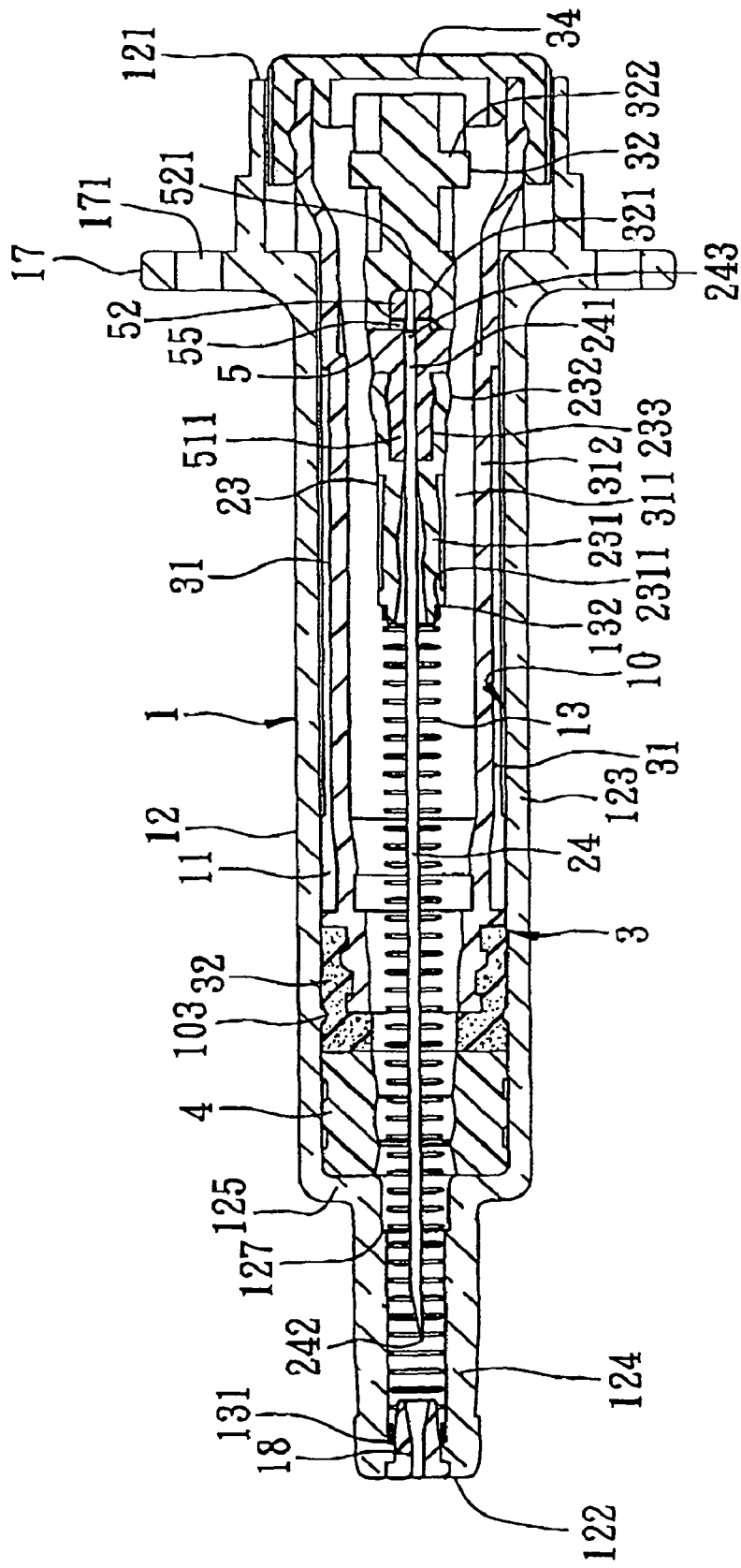
FIG. 7 is a sectional view of the first preferred embodiment in a retracted state.

With reference to FIGS. 6 and 7, a pushing force is further applied to the plunger body 31 to push the grip unit 4 forward against the first and second frictional forces (i.e., the frictional engagement between the grip unit 4 and the bushing unit 10) such that the front hub portion 231 of the needle seat 23 moves past the friction diminishing area 129 to abut against the first shoulder abutment 127, thereby facilitating a triggering action for retraction of the needle cannula 24 (to be described in detail hereinafter). Hence, the movement of the front hub portion 231 results in reduced friction between the front hub portion 231 and the smaller-diameter portion 124 of the barrel 1.

Subsequently, the needle seat 23 and the shield plug member 5 remain unmoved and stay in place due to the abutment of the front hub portion 231 against the first shoulder abutment 127. Once the plunger 3 is pressed further forward to cause movement of the plunger body 31 relative to the coupling member 32 against the third frictional force, the retained portion 322 is released from the intermediate surrounding wall 312. Thus, the shield plug member 5 is moved with the coupling member 32 by the biasing action of the coil spring 13 to a retracted position, where the coupling member 32 is disposed closer to the rear opened end wall 314 and where the needle seat 23, the shield plug member 5 and the needle cannula 24 are received in the accommodation chamber 311. Furthermore, when the retained portion 322 is released from the intermediate surrounding wall 312, the needle seat 23 and the shield plug member 5, together with the needle cannula 24, will be moved with the coupling member 32, which is suctioned into the accommodation chamber 311 due to a pressure difference between the reduced pressure in the accommodation chamber 311 and the ambient air. It is noted that the needle cannula 24 may be retracted into the accommodation chamber 311 only by the pressure difference in case the coil spring 13 is not provided.

Referring to FIGS. 8 and 9, the second preferred embodiment of a disposable syringe according to this invention is similar to the first preferred embodiment in construction and function. In this embodiment, the barrel 1 is made from a glass material. A bushing sleeve 19, which is made from a thermoplastic material, is disposed on the smaller-diameter portion 124 of the barrel 1. The first shoulder abutment 127 is formed on the bushing sleeve 19. The bushing sleeve 19 further has an annular abutment 192 which is disposed adjacent to the forward opening 122 of the barrel 1 and which confronts the front end wall 2311 of the needle seat 23 such that the coil spring 13 is disposed between and abuts against the annular abutment 192 and the front end wall 2311. Since the bushing sleeve 19 is made from a thermoplastic material, it can be easily formed to have a desired dimension and shape. Thus, the assembly of the coil spring 13 is efficient to conduct to facilitate manufacture of the disposable syringes at relatively low cost.

Figure 11:
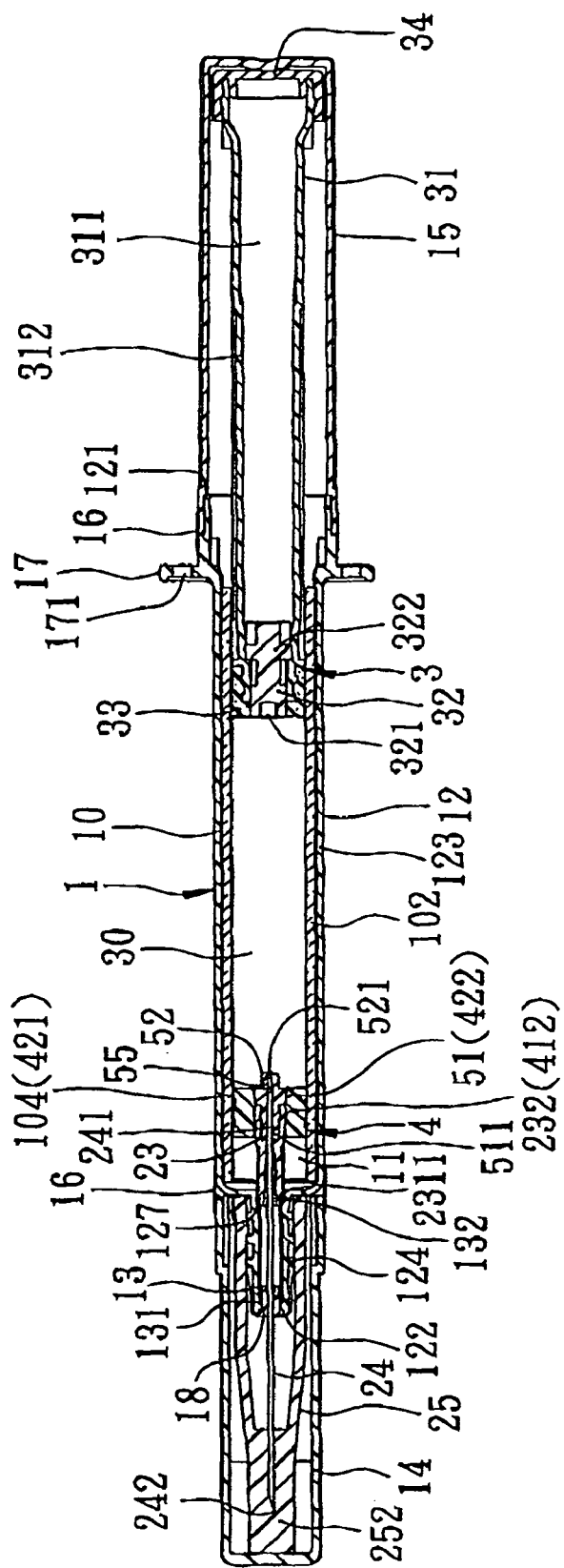
FIGS. 11 and 12 are sectional views of the third preferred embodiment in a state of use and in a retracted state, respectively.
Figure 12:
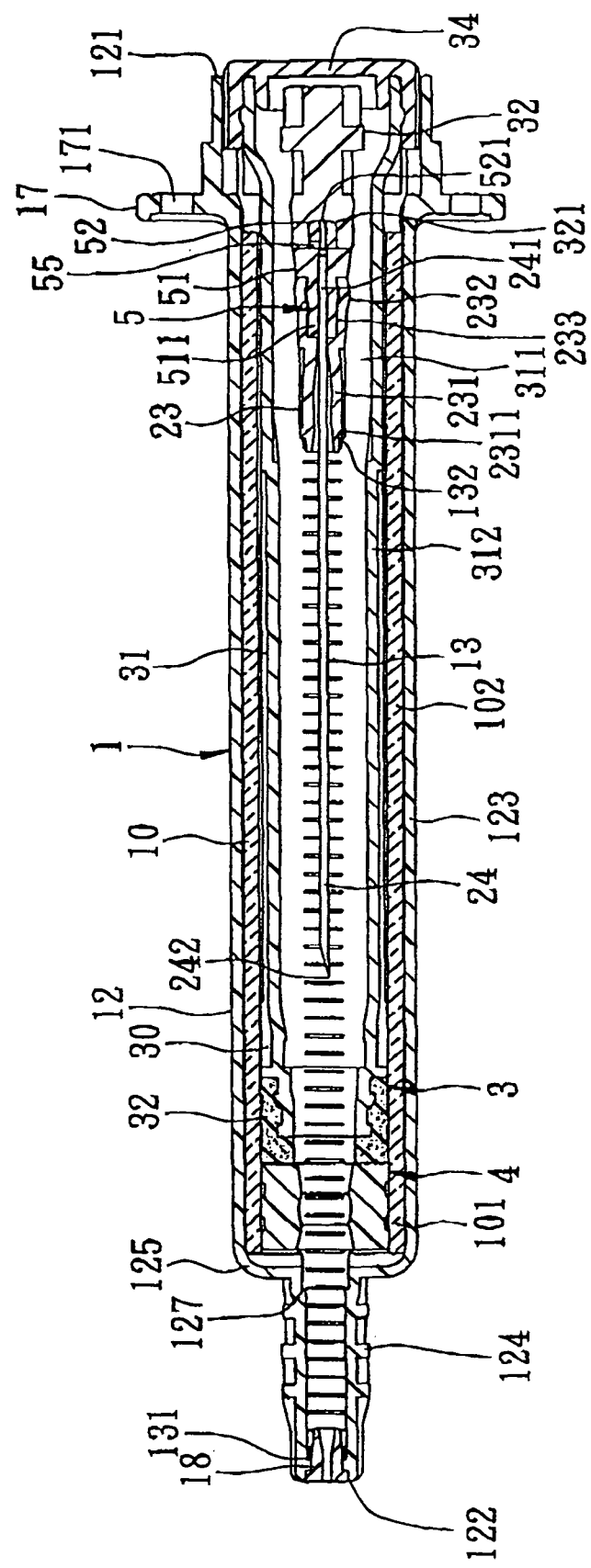

Referring to FIGS. 10 to 12, the third preferred embodiment of a disposable syringe according to this invention is similar to the first preferred embodiment in construction and function. In this embodiment, the barrel 1 is made from a thermoplastic material. The bushing unit 10 is made from a material which is more chemically resistant than that of the barrel 1, such as a glass material. Since the medicament contained in the medicament chamber 30 comes into contact with the bushing unit 10, rather than the barrel 1, and is maintained in an air-tight and water-tight state by the coupling member 32, the seal ring 33, the grip unit 4, and the shield plug member 5, the medicament will not be degraded, and the manufacturing cost of the disposable syringe can be reduced.

Figure 13:
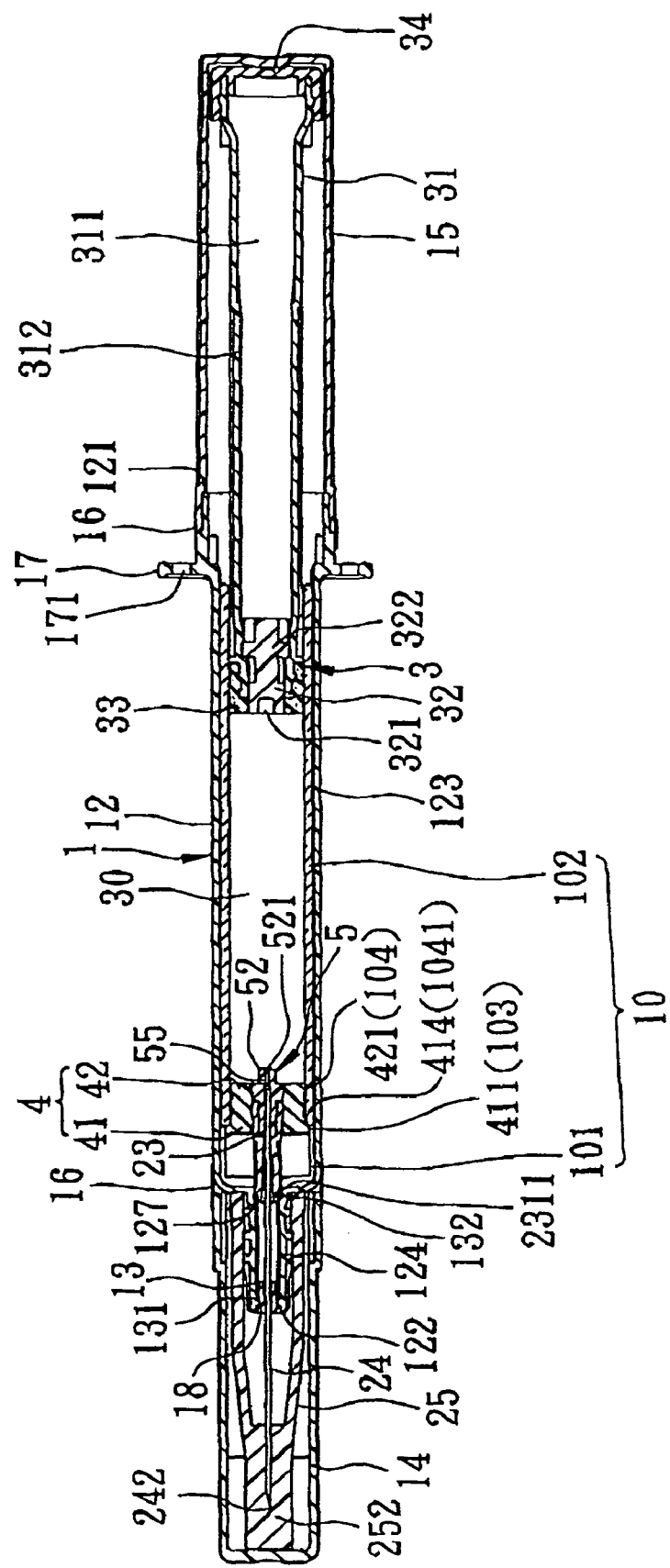
FIG. 13 is a sectional view of the fourth preferred embodiment of a disposable syringe according to this invention.

Referring to FIG. 13, the fourth preferred embodiment of a disposable syringe according to this invention is similar to the third preferred embodiment in construction and function. In this embodiment, the front bushing member 101 is integrally formed with the barrel 1, and has an inner diameter larger than that of the rear bushing member 102. The rear retaining segment 104 of the rear bushing member 102 has an end edge 1041 which abuts against the front bushing member 101. In addition, the front grip member 41 has a shoulder 414 which confronts rearwardly, which is formed between the front and rear outer surrounding retained surfaces 411,421, and which abuts against the end edge 1041 of the rear retaining segment 104 in the position of use to thereby guard against undesired rearward movement of the grip unit 4 during transportation of the disposable syringe, a needle piercing process, etc., for example.

Figure 14:
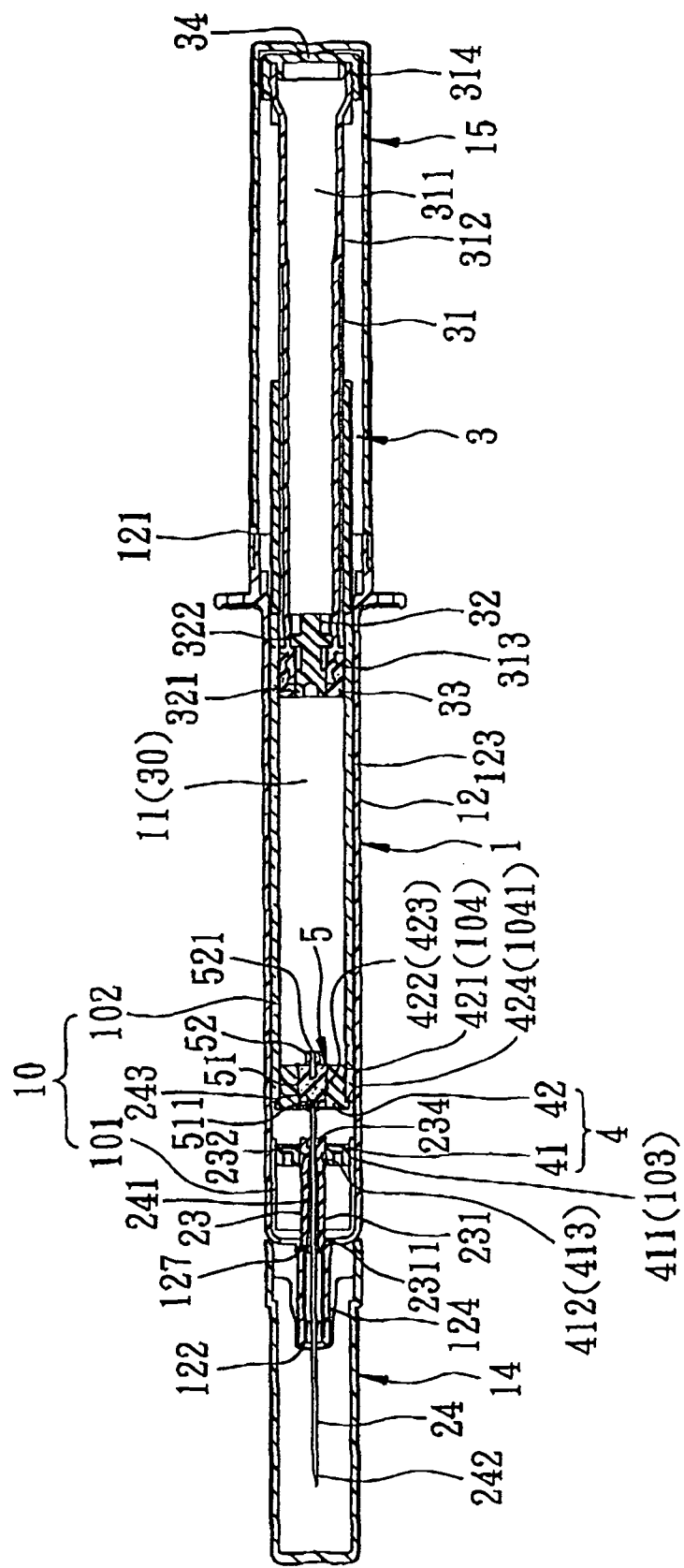
FIGS. 14 and 15 are sectional views of the fifth preferred embodiment of a disposable syringe according to this invention in a pre-used state and a state of use, respectively.
Figure 15:
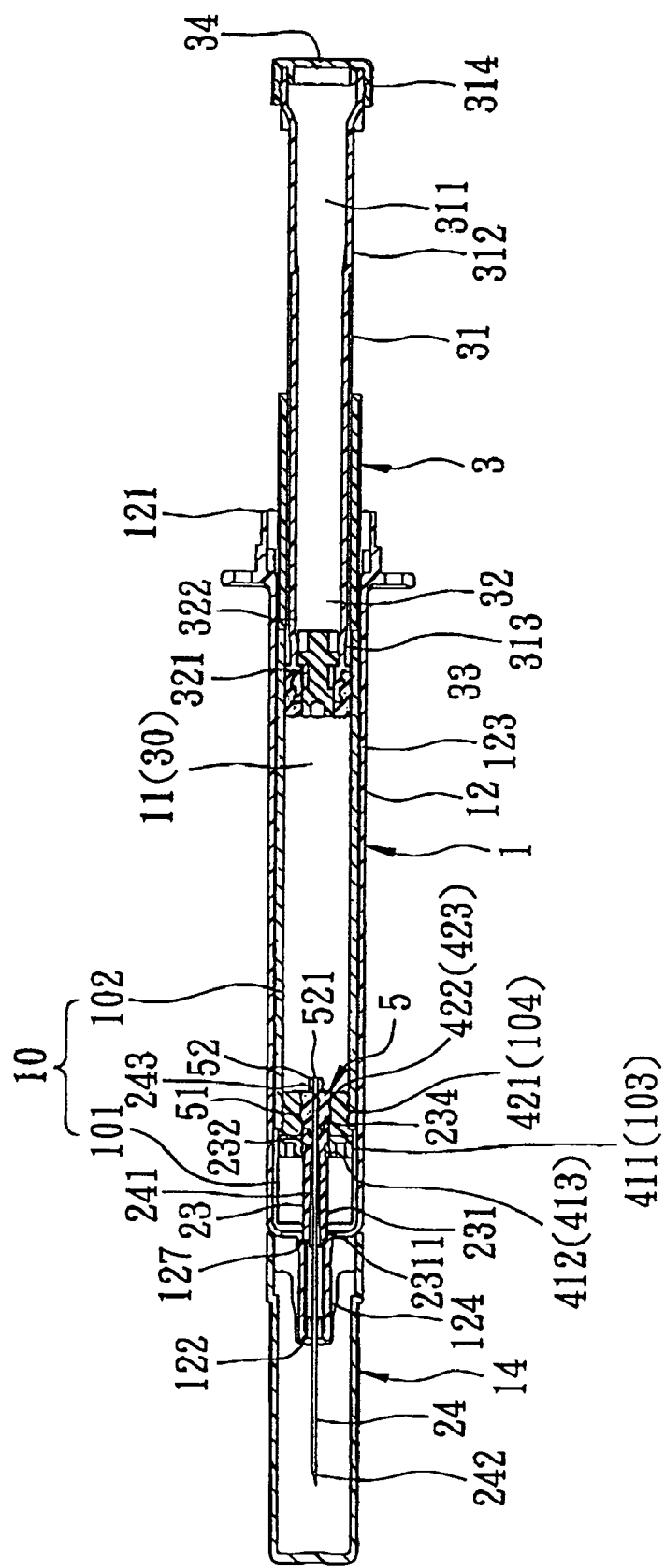

Referring to FIGS. 14 and 15, the fifth preferred embodiment of a disposable syringe according to this invention is similar to the first preferred embodiment in construction and function. In this embodiment, the rear bushing member 102 is made from a chemically resistant material, such as glass, a cyclic olefin polymer, or the like, and is separated from the front bushing member 101. The front bushing member 101 may be integrally formed with the larger-diameter portion 123 of the barrel 1 and may be made from a thermoplastic material. Moreover, the rear grip member 42 has a flange 424 which extends radially and outwardly from the rear outer surrounding retained surface 421 and which abuts against an end edge 1041 of the rear retaining segment 104 in the position of use to thereby guard against undesired rearward movement of the rear grip member 42.

Specifically, in a pre-use position as shown in FIG. 14, the rear bushing member 102 and the rear grip member 42 are respectively spaced apart from the front bushing member 101 and the front grip member 41 in the axial direction. When the disposable syringe is moved from the pre-use position to the position of use, as shown in FIG. 15, the rear bushing member 102 and the rear grip member 42 are respectively brought to engage the front bushing member 101 and the front grip member 41. Specifically, once the rear grip member 42 is brought to engage the front grip member 41, the embedded end 234 is brought to engage with the plug body 51 in the rear bore 423 to permit the communicating end 243 of the needle cannula 24 to pierce through the plug body 51 so as to reach the duct 521.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

We claim:
1. A disposable syringe comprising:
a barrel having a surrounding barrel wall which surrounds an axis in an axial direction, and which defines a passage therein, said passage having rearward and forward openings which are disposed opposite to each other in the axial direction, said surrounding barrel wall including a larger-diameter portion and a smaller-diameter portion which are disposed proximate to said rearward and forward openings, respectively, and a first shoulder abutment which is disposed on said smaller-diameter portion and which confronts rearwardly;
a bushing unit which is disposed on said larger-diameter portion, and which includes front and rear bushing members that are respectively proximate to and distal from said first shoulder abutment, and that extend towards each other to terminate at front and rear retaining segments, respectively;
a needle cannula which extends along the axis and which has a fixed segment that extends in said passage to terminate at a communicating end, and a tip end extending forwardly of said forward opening;
a tubular grip unit including
    front and rear grip members which are opposite to each other in the axial direction, which respectively have front and rear outer surrounding retained surfaces that, in a position of use, are respectively in fluid-tight engagement with said front and rear retaining segments by virtue of first and second frictional forces, respectively, and which respectively have front and rear inner surrounding grip surfaces that extend along the axis to define front and rear bores, respectively;
a tubular needle seat including a front hub portion which is disposed to fix said needle cannula therein and which has a front end wall that confronts said first shoulder abutment, and a rear gripped portion extending from said front hub portion in the axial direction to terminate at an embedded end, said rear gripped portion being inserted into said front bore, and being in frictional engagement with said front inner surrounding grip surface;
a shield plug member which is made from a material different from that of said tubular needle seat, and which is inserted into said rear bore, said shield plug member including
    a plug body which extends forwardly to terminate at a dock end that admits entry of said communicating end of said needle cannula, and which is configured to stuff said rear bore such that said plug body is in fluid-tight engagement with said rear inner surrounding grip surface, and
    an anchored end which extends rearwardly from said plug body, and which has a duct configured to extend in the axial direction to permit fluid communication between said anchored end and said communicating end in the position of use; and
a tubular plunger which is disposed to be movable along said passage in said bushing unit, said plunger including
    a plunger body having front and rear opened end walls which are disposed opposite to each other along the axis, said rear opened end wall extending outwardly of said rearward opening so as to be manually operable, said plunger body further having an intermediate surrounding wall which is interposed between said front and rear opened end walls and which defines an accommodation chamber, a seal ring which is made from a deformable material, which is sleeved retainingly on said front opened end wall, and which is slidable on and in fluid-tight frictional engagement with said rear bushing member so as to cooperate with said rear grip member to define, in said bushing unit, a medicament chamber that is communicated with said duct, and a coupling member which has a retained portion that extends along the axis and that is disposed in said accommodation chamber to be in frictional engagement with said intermediate surrounding wall by virtue of a third frictional force, and an anchoring portion that extends from said retained portion forwardly to be engageable with said anchored end when said coupling member is moved forwardly such that, when said front and rear grip members are pushed forward by virtue of forward movement of said plunger against the first and second frictional forces in the position of use, said anchoring portion is brought to mate with said anchored end, which remains unmoved and stays in place due to abutment of said front hub portion against said first shoulder abutment, and such that, once said plunger is moved further forward to cause movement of said plunger body relative to said coupling member against the third frictional force, said retained portion is released from said intermediate surrounding wall to thereby permit movement of said anchored end with said anchoring portion to a retracted position, where said anchoring portion is disposed closer to said rear opened end wall and where said needle seat, said shield plug member and said needle cannula are received in said accommodation chamber.

2. The disposable syringe according to claim 1, wherein said anchoring portion is in form of a socket, said anchored end being in form of a plug which is configured to mate with said socket, and which is disposed rearwardly and outwardly of said rear grip member, said anchored end being provided with a radial inlet which extends radially to communicate said medicament chamber with said duct, and which is disposed adjacent to said rear grip member such that said radial inlet remains open when said socket is brought to substantially engage said plug, thereby interrupting axial communication between said duct and said medicament chamber.

3. The disposable syringe according to claim 1, wherein said bushing unit and said grip unit are disposed such that, in a pre-use position, said rear bushing member and said rear grip member are respectively spaced apart from said front bushing member and said front grip member in the axial direction, and such that said rear bushing member and said rear grip member are respectively brought to engage said front bushing member and said front grip member so as to place the disposable syringe in the position of use.

4. The disposable syringe according to claim 3, wherein, once said rear grip member is brought to engage said front grip member, said embedded end is brought to engage with said plug body in said rear bore to permit said communicating end of said needle cannula to pierce through said plug body so as to be in fluid communication with said duct.

5. The disposable syringe according to claim 4, wherein said rear bushing member is made from a material which is more chemically resistant than that of said barrel, said rear grip member having a flange which extends radially and outwardly from said rear outer surrounding retained surface and which abuts against an end edge of said rear retaining segment in the position of use to thereby guard against rearward movement of said rear grip member.

6. The disposable syringe according to claim 1, wherein said front and rear bushing members are integrally formed with each other to constitute said bushing unit, and said front and rear grip members are integrally formed with each other to constitute said tubular grip unit.

7. The disposable syringe according to claim 6, wherein said embedded end is disposed to engage said dock end in said rear bore, and said communicating end is in fluid communication with said duct.

8. The disposable syringe according to claim 7, wherein said bushing unit is integrally formed with said larger-diameter portion.

9. The disposable syringe according to claim 1, wherein said front grip member has a shoulder which confronts rearwardly, which is formed between said front and rear outer surrounding retained surface, and which abuts against an end edge of said rear retaining segment in the position of use to thereby guard against rearward movement of said grip unit.

10. The disposable syringe according to claim 1, wherein said surrounding barrel wall has a second shoulder abutment which is formed between said smaller-diameter portion and said larger-diameter portion, and which confronts forwardly, said larger-diameter portion having a third shoulder abutment which is disposed adjacent to said rearward opening and which confronts rearwardly, said disposable syringe further comprising:
    a front protector which is detachably sleeved on said smaller-diameter portion and which abuts against said second shoulder abutment for shielding said needle cannula;
    a rear protector which is detachably sleeved on said larger-diameter portion and which abuts against said third shoulder abutment for shielding said plunger; and
    a front sealing strip which is disposed to peelably adhere said front protector to said second shoulder abutment; and
    a rear sealing strip which is disposed to peelably adhere said rear protector to said larger-diameter portion.

11. The disposable syringe according to claim 10, further comprising an air-tight sleeve which is removably sleeved on said smaller-diameter portion to shield said needle cannula and which has an elastomeric front end, said tip end of said needle cannula being trapped in said elastomeric front end.

12. The disposable syringe according to claim 11, wherein said elastomeric front end is threadedly engaged with said front protector.

13. The disposable syringe according to claim 1, wherein said smaller-diameter portion has a friction diminishing area which is disposed between said first shoulder abutment and said front hub portion such that, when said grip unit is pushed forward by virtue of the forward movement of said plunger against the first and second frictional forces, said front hub portion is moved past said friction diminishing area to abut against said first shoulder abutment to thereby facilitate a triggering action for retraction of said needle cannula.

14. The disposable syringe according to claim 1, further comprising a coil spring which is disposed within said smaller-diameter portion, which abuts against said front end wall, and which surrounds said needle cannula so as to bias said needle seat, together with said shield plug member, to move towards the retracted position.

15. The disposable syringe according to claim 14, wherein said barrel includes a bushing sleeve which is disposed on said smaller-diameter portion and which has said first shoulder abutment and an annular abutment that is disposed adjacent to said forward opening and that confronts said front end wall of said needle seat such that said coil spring is disposed between and abuts against said annular abutment and said front end wall.

16. The disposable syringe according to claim 1, wherein said accommodation chamber contains a fluid at a reduced pressure such that, once said retained portion is released from said intermediate surrounding wall and said needle seat and said shield plug member, together with said needle cannula, will be moved with said coupling member, which is suctioned into said accommodation chamber due to a pressure difference between the reduced pressure the ambient air.

17. The disposable syringe according to claim 1, further comprising a tubular holding member which is inserted into said passage from said forward opening, which is fitted to said smaller-diameter portion, and which is configured to hold said needle cannula in the position of use.

18. The disposable syringe according to claim 1, wherein said rear bushing member is made from a material selected from a group consisting of glass and a cyclic olefin polymer.

19. The disposable syringe according to claim 1, wherein said bushing unit is made from a material which is more chemically resistant than that of said barrel.

20. The disposable syringe according to claim 1, wherein said barrel has a pair of lugs which extend radially and outwardly from said larger-diameter portion adjacent to said rearward opening for gripping by fingers of a user and which has anchor holes for anchoring a marked tab.

* * * * *